United States Patent
Keary et al.

(10) Patent No.: US 6,294,008 B1
(45) Date of Patent: Sep. 25, 2001

(54) HAZE-FREE CELLULOSE ETHER CAPSULES AND PROCESS FOR MAKING

(75) Inventors: Colin M. Keary; Gary J. Schulz, both of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/295,692

(22) Filed: Apr. 21, 1999

(51) Int. Cl.⁷ ............... C09D 101/26; C09D 101/28; C08B 11/20; B28B 1/38
(52) U.S. Cl. ............... 106/172.1; 106/198.1; 536/85; 536/86; 536/88; 536/89; 264/301
(58) Field of Search ............... 106/172.1, 198.1; 536/85, 86, 88, 89; 264/301

(56) References Cited

U.S. PATENT DOCUMENTS

| | | | |
|---|---|---|---|
| 3,391,135 | 7/1968 | Ouno et al. | 260/214 |
| 4,001,211 | 1/1977 | Sarker | 536/84 |
| 4,229,572 * | 10/1980 | Zweigle | 536/89 |
| 4,339,574 * | 7/1982 | Wust et al. | 536/84 |
| 4,364,836 * | 12/1982 | Ziche | 252/135 |
| 4,398,024 * | 8/1983 | Bernert et al. | 536/85 |
| 4,404,370 * | 9/1983 | Bernert et al. | 536/85 |
| 4,988,807 | 1/1991 | Christensen et al. | 536/127 |
| 5,218,107 | 6/1993 | Schulz | 536/84 |
| 5,264,223 | 11/1993 | Yamamoto et al. | 424/451 |
| 5,431,917 | 7/1995 | Yamamoto et al. | 424/451 |
| 5,543,162 | 8/1996 | Timonen et al. | 426/89 |
| 5,591,455 | 1/1997 | Signorino | 424/490 |
| 5,840,882 | 11/1998 | Doenges et al. | 536/91 |

FOREIGN PATENT DOCUMENTS

| | | | |
|---|---|---|---|
| 41 12 849 | 10/1991 | (DE) | C08B/11/08 |
| 0 210 917 | 2/1987 | (EP) | C08B/11/20 |

* cited by examiner

Primary Examiner—David Brunsman

(57) ABSTRACT

Disclosed is a cellulose ether composition having a low molecular weight cellulose ether of a viscosity of about 200 centipoise or less in a two percent aqueous solution at 20° C. The composition has a sodium chloride content of about 0.3 weight percent or less based upon the weight of the cellulose ether. The composition exhibits significantly reduced haze formation when in capsule form. Also disclosed is a process for making the composition.

20 Claims, No Drawings

HAZE-FREE CELLULOSE ETHER CAPSULES AND PROCESS FOR MAKING

FIELD OF THE INVENTION

The present invention relates to haze-free cellulose ether capsules and a process for making. The capsules are useful in pharmaceutical applications.

BACKGROUND OF THE INVENTION

Cellulose ethers are commonly employed commercially to form capsules which are adapted to contain and orally deliver pharmaceutical agents and medicaments. Preferred cellulose ethers for such applications are methylcellulose and hydroxypropylmethylcellulose.

Cellulose ether capsules are typically manufactured by dipping hot pins in a cold, aqueous cellulose ether dip coating solution. The solution gels on the pins and water evaporates during a drying step to form thin film layers of dried cellulose ether around the hot pins. The thin films take the form of caps and bodies, which are then removed from the pins. Caps are mated with bodies to form capsules. Analogous processes exist wherein cold pins are dipped in a hot, aqueous cellulose ether solution. Processes for making capsules are seen in U.S. Pat. Nos. 3,617,588;4,001,211;4,917,885; and 5,756,036, which are incorporated herein by reference.

A problem commonly encountered in manufacturing cellulose ether capsules is haze formation at their inner surfaces. Haze formation is most noticeable in transparent capsules.

Haze causes cellulose ether capsules to exhibit less luster and gloss than they would otherwise. Due to haze, cellulose ether capsules typically do not have the same level of luster as gelatin capsules. This difference in appearance is discussed in "HPMC Capsules—An Alternative to Gelatin," *Pharmaceutical Technology Europe* 10(11) (1998).

It would be desirable to have cellulose ether capsules which are substantially free of haze formation at their interior surfaces and a process for making such capsules. It would also be desirable to have a process for making a cellulose ether composition useful in such capsules.

SUMMARY OF THE INVENTION

According to the present invention, there is a cellulose ether composition comprising a low molecular weight cellulose ether. The composition has a sodium chloride content of about 0.3 weight percent or less based upon the weight of the cellulose ether. The composition exhibits significantly reduced haze formation when in capsule form. Useful embodiments also include aqueous and capsule forms of the composition.

Further according to the present invention, there is a process for making a cellulose ether composition. The process comprises a) alkalyzing a cellulose pulp by contacting it with sodium hydroxide; b) etherifying the cellulose pulp to form a cellulose ether; c) washing the cellulose ether to reduce sodium chloride content; d) drying the cellulose ether to a reduced moisture content; e) milling the cellulose ether to a particulate form; f) contacting the particulate cellulose ether with an amount of hydrogen chloride sufficient to partially depolymerize it such that a two percent aqueous solution of it has a viscosity of 200 cP or less at 20° C.; g) partially or substantially neutralizing the acid by contacting with a sodium compound. The cellulose ether is washed to a sufficient extent and the amount of hydrogen chloride employed is adjusted to a sufficient extent to limit the sodium chloride content of the depolymerized cellulose ether to about 0.3 weight percent or less based upon the weight of the depolymerized cellulose ether.

Further according to the present invention, there is a process for making cellulose ether capsules from the cellulose ether composition having low sodium chloride content. The cellulose ether is dissolved in water to form a dip coating solution. Metal pins are dipped into the coating solution. The solution is allowed to gel and subsequently dry on the pins to form thin films of dried cellulose ether around the pins. The thin films takes the form of caps and/or bodies which are then removed from the pins. The caps and/or bodies can subsequently be mated to form whole capsules. Both hot pin/cold solution and cold pin/hot solution processes are contemplated.

DETAILED DESCRIPTION

In the present invention, it was discovered that haze formation in cellulose ether capsules can be significantly reduced by limiting the amount of sodium chloride remaining in the depolymerized end product from which the capsules are formed. The amount of sodium chloride remaining in the end product can be controlled by the following two methods: i) washing the cellulose ether following etherification and prior to milling to reduce sodium chloride content and ii) limiting the amount of hydrogen chloride employed in the depolymerization reactor to limit and preferably minimize the amount of sodium chloride byproduct produced. Substeps i) and ii) are employed to an extent sufficient to reduce the sodium chloride content of the depolymerized cellulose ether end product to about 0.3 weight percent or less and most preferably about 0.15 weight percent or less based upon the weight of the depolymerized cellulose ether.

Generally, low molecular weight cellulose ethers are produced by alkalyzing or causticizing a cellulose pulp and etherifying it to form a high molecular weight cellulose ether, which is then depolymerized to form a low molecular weight cellulose ether. High molecular weight cellulose ethers have viscosities of up to about 100,000 centipoise (cP) in a 2 percent aqueous solution at 20° C.

Low molecular weight cellulose ethers have viscosities of about 200 cP or less in a 2 percent aqueous solution at 20° C. Viscosities are determined according to ASTM D1347 and D2363.

Cellulose pulp is alkalyzed or causticized in a reactor with an alkaline hydroxide, preferably sodium hydroxide. The pulp may be alkalyzed by any means known in the art such as steeping in a bath or stirred tank or by spraying directly on dry pulp. The headspace of the reactor may be evacuated or purged with an inert gas to control depolymerization of the cellulose ether product.

The alkylated cellulose pulp is then etherified to form cellulose ethers of preferably up to about 100,000 cP in a 2 percent aqueous solution at 20° C. Typical etherifying agents include the lower alkyl halides such as methyl chloride and ethyl chloride and epoxides such as ethylene oxide, propylene oxide, and butylene oxide. For instance, methyl chloride may be used to make methylcellulose and a mixture of methyl chloride and propylene oxide may be used to make hydroxypropylmethylcellulose. The use of methyl chloride with sodium hydroxide as an alkalyzing agent results in the by-product formation of sodium chloride (salt). If desired, a diluent such as dimethyl ether may be employed during etherification.

The cellulose ether is washed to remove salt and other reaction by-products. Washing is employed in conjunction with control of the amount of hydrogen chloride used in the depolymerization reaction (see below) to minimize residual salt content in the depolymerized cellulose ether end product. Any solvent in which salt is soluble may be employed, but water is highly preferred. The cellulose ether may be washed in the etherification reactor but is preferably washed in a separate washer located downstream of that reactor. Process washing variables which impact residual salt content in the cellulose ether include washing residence time, salt content of wash solvent (water), and multiple washings. Residual salt content is most effectively controlled by multiple washings, with two separate washings usually being sufficient. Before or after washing, the cellulose ether may be stripped by exposure to steam to further reduce residual organic content.

The washed cellulose ether is then dried to a reduced moisture content of about 0.5 to about 5.0 weight percent water and preferably about 0.8 to about 3.0 weight percent water based upon the weight of cellulose ether. Useful dryers include tray dryers, fluid bed dryers, flash dryers, agitation dryers, and tube dryers.

The cellulose ether is milled to particulates of desired size. If desired, the cellulose ether may be milled and dried simultaneously. Milling may be accomplished by any means known in the art such as a ball mill or an impact pulverizer.

The milled particulates of high molecular weight cellulose ether are depolymerized to form particulate low molecular weight cellulose ethers. Depolymerized low molecular weight cellulose ethers typically have molecular weights such that a two percent aqueous solution at 20° C. has a viscosity of about 200 cP or less, preferably about 1 to about 100 cP, and more preferably about 3 to about 100 cp. Cellulose ethers usually employed in making pharmaceutical capsules and coatings have viscosities of about 3 to about 15 cP in a two percent aqueous solution at 20° C.

In preparation for depolymerization, the cellulose ether particulates are heated to a temperature of about 50° C. to about 130° C. and preferably about 60° C. to about 100° C. The heating may be accomplished in the depolymerization reactor or by a separate heater upstream of such reactor. The moisture content of the particulates can be restored, if necessary, to a higher level prior to depolymerization by blending the particulates with water in the depolymerization reactor or a separate mixer upstream of such reactor.

The milled cellulose ether particulates are depolymerized by contacting or treating them with a strong acid, preferably anhydrous hydrogen chloride. The acid can be added to the headspace of the reactor or directly into the cellulose ether powder. The headspace of the reactor may be purged with an inert gas to prevent combustion or ignition of the powder.

Following depolymerization, the particulate cellulose ether is contacted with a basic sodium compound, preferably a substantially anhydrous compound such as sodium bicarbonate, to partially or substantially neutralize any remaining acid. A preferred method of neutralizing is blowing the compound into the headspace or interior of the depolymerization reactor or other vessel where the depolymerized particulate cellulose ether may be situated. The depolymerization reactor or other vessel is preferably tumbled during neutralization to ensure uniform contact with the internal surfaces of the reactor.

To minimize or limit the amount of sodium chloride by-product produced during neutralization, the amount (concentration) of hydrogen chloride employed to catalyze the depolymerization reaction is set at relatively low levels and is preferably minimized. Amount (concentration) of hydrogen chloride and reaction temperature substantially govern reaction rate. Losses in reaction rate due to reduction in the amount of hydrogen chloride employed can be compensated for by increasing reaction temperature or by increasing reaction time. Given that increases in reaction time reduce production efficiencies and raise economic costs, it is most desirable to increase reaction temperatures to make up for relatively lesser amounts of hydrogen chloride. Conventionally, depolymerization reaction temperatures have ranged from about 50° C. to about 130° C. and more typically from about 60° C. to about 100° C. To increase reaction time, higher reaction temperatures of about 80° C. to about 110° C. are most preferred in the present invention. In a preferred embodiment, hydrogen chloride is added to the depolymerization reactor at about 0.10 to about 0.19 weight percent based upon the weight of the cellulose ether to be depolymerized.

Useful teachings relating to making low molecular weight cellulose ethers are seen in U.S. Ser. No. 09/203,324, filed Dec. 1, 1998, which is incorporated herein by reference.

The present process is useful for making the following cellulose ethers: methylcellulose, hydroxyethylmethylcellulose, hydroxypropylmethylcellulose, and hydroxybutylmethylcellulose. The process is particularly useful in making methylcellulose and hydroxypropylmethylcellulose.

The low molecular weight cellulose ethers are useful in other pharmaceutical applications such as tablet coatings and as excipients for pharmaceutical agents and medicaments in capsules and tablets. Other useful applications include building products and food applications.

While embodiments of the capsule process and process of the present invention have been shown with regard to specific details, it will be appreciated that the present invention may be modified while still being fairly within the scope of the novel teachings and principles set forth herein.

What is claimed is:

1. A cellulose ether composition, the composition comprising a low molecular weight cellulose ether having a viscosity of 200 centipoise or less in a two percent aqueous solution at 20° C., the composition having a sodium chloride content of about 0.3 weight percent or less based upon the weight of the cellulose ether.

2. The composition of claim 1, the composition having a sodium chloride content of about 0.15 weight percent or less based upon the weight of the cellulose ether.

3. The composition of claim 1, the cellulose ether comprising methylcellulose or hydroxypropylmethylcellulose.

4. The composition of claim 3, wherein the viscosity is about 3 to about 15 cP, the composition taking the form of a capsule.

5. The composition of claim 4, wherein the composition has a content of about 0.15 weight percent sodium chloride or less based upon the weight of the cellulose ether.

6. The composition of claim 1, the composition taking the form of an aqueous composition.

7. The composition of claim 1, the composition taking the form of a capsule.

8. The composition of claim 1, wherein the viscosity is about 3 to about 100 cP.

9. The composition of claim 1, wherein the viscosity is about 3 to about 15 cP.

10. A process for making a cellulose ether composition, the process comprising:

a) alkalyzing a cellulose pulp by contacting it with sodium hydroxide;

b) etherifying the cellulose pulp to form a cellulose ether;

c) washing the cellulose ether to reduce sodium chloride content;

d) drying the cellulose ether to a reduced moisture content;

e) milling the cellulose ether to a particulate form;

f) contacting the particulate cellulose ether with an amount of hydrogen chloride sufficient to partially depolymerize it such that a two percent aqueous solution of it has a viscosity of 200 cP or less at 20° C.;

g) partially or substantially neutralizing the hydrogen chloride by contacting the particulate cellulose ether with a basic sodium compound, the cellulose ether being washed in step c) to an extent and the amount of hydrogen chloride being adjusted in step f) to an extent sufficient to limit the sodium chloride content of the depolymerized cellulose ether to about 0.3 weight percent or less based upon the weight of the depolymerized cellulose ether.

11. The process of claim 10, wherein the depolymerized cellulose ether is dissolved in water to form a dip coating solution, metal pins being dipped into the coating solution, the metal pins being removed from the coating solution, the solution being allowed to gel and subsequently dry on the surface of the pins to form caps and/or bodies, and the caps and/or bodies being removed from the pins.

12. The process of claim 11, wherein the sodium compound is sodium bicarbonate.

13. The process of claim 11, wherein the cellulose ether is a methylcellulose or a hydroxypropylmethylcellulose.

14. The process of claim 10, wherein the sodium compound is sodium bicarbonate.

15. The process of claim 10, wherein the cellulose ether is a methylcellulose or a hydroxypropylmethylcellulose.

16. The process of claim 10, wherein the particulate cellulose ether is depolymerized at a temperature of about 50° C. to about 130° C.

17. The process of claim 10, wherein the particulate cellulose ether is depolymerized at a temperature of about 80° C. to about 110° C.

18. The process of claim 17, wherein the amount of hydrogen chloride employed is about 0.10 to about 0.19 weight percent based upon the weight of the cellulose ether.

19. The process of claim 10, wherein the amount of hydrogen chloride employed is about 0.10 to about 0.19 weight percent based upon the weight of the cellulose ether.

20. The process of claim 10, wherein the sodium compound is sodium bicarbonate, the cellulose ether being a methylcellulose or a hydroxypropylmethylcellulose, the particulate cellulose ether being depolymerized at a temperature of about 80° C. to about 110° C., the amount of hydrogen chloride employed being about 0.10 to about 0.19 weight percent based upon the weight of the particulate cellulose ether to be depolymerized.

\* \* \* \* \*